United States Patent [19]

Dancoine

[11] Patent Number: 4,616,515

[45] Date of Patent: Oct. 14, 1986

[54] PROCESS AND DEVICE FOR AUTOMATIC SAMPLING OF BULK MATERIALS CONTAINED IN TRANSPORT VEHICLES

[76] Inventor: Daniel Dancoine, Herbaudiere de Saivres par, Saint-Maixent L'Ecole - 79400, France

[21] Appl. No.: 642,357

[22] Filed: Aug. 20, 1984

[30] Foreign Application Priority Data

Aug. 19, 1983 [FR] France ............................ 83 13469

[51] Int. Cl.$^4$ .......................... G01N 1/08; G01N 1/14; G01N 1/18
[52] U.S. Cl. ................................ 73/864.31; 73/863.01; 73/863.23; 73/863.82; 73/863.83; 73/864.34; 73/864.45
[58] Field of Search ........... 73/864.31, 864.33, 864.34, 73/863.01, 863.23, 863.82, 863.83, 864.45

[56] References Cited

U.S. PATENT DOCUMENTS

| | | | |
|---|---|---|---|
| 2,771,776 | 11/1956 | Haven ............................. | 73/864.33 |
| 3,158,030 | 11/1964 | Cross ............................... | 73/864.31 |
| 3,580,084 | 5/1971 | Kramer ............................ | 73/864.33 |
| 3,683,702 | 8/1972 | O'Brien et al. ................. | 73/864.31 X |
| 3,724,276 | 4/1973 | Schwind ......................... | 73/864.34 |
| 3,786,682 | 1/1974 | Winter et al. .................. | 73/864.33 X |
| 3,822,597 | 7/1974 | Clark .............................. | 73/864.31 X |
| 3,954,013 | 5/1976 | West ............................... | 73/864.31 X |
| 3,998,102 | 12/1976 | Santorilla ...................... | 73/863.82 |
| 4,003,260 | 1/1977 | Catoul .......................... | 73/864.31 X |
| 4,037,476 | 7/1977 | McCrabb . | |
| 4,179,929 | 12/1979 | Redding ......................... | 73/864.31 |
| 4,483,205 | 11/1985 | Bellaiche et al. ............. | 73/863.23 |

FOREIGN PATENT DOCUMENTS

| | | | |
|---|---|---|---|
| 897199 | 5/1962 | United Kingdom ............. | 73/863.82 |
| 463026 | 5/1975 | U.S.S.R. ............................ | 73/864.31 |
| 560160 | 5/1977 | U.S.S.R. ............................ | 73/864.31 |

*Primary Examiner*—Stewart J. Levy
*Assistant Examiner*—Tom Noland
*Attorney, Agent, or Firm*—Sandler & Greenblum

[57] ABSTRACT

A process and device for automatic sampling includes a travelling gantry under which a vehicle can be brought carrying a tank containing the product to be tested. The gantry includes an upper horizontal beam which includes a carriage enabling the support and horizontal movement of a sampling probe. The sampling probe is put under low pressure by an aspirator in order to draw the product towards a receiver. The gantry also includes a sampler device for the product connected to the receiver. The various parts are carried by the gantry and connected to a control desk. The device is used notably for the sampling of milk products, flours, cements, liquid chemical products, wines, oils and fuels.

25 Claims, 1 Drawing Figure

PROCESS AND DEVICE FOR AUTOMATIC SAMPLING OF BULK MATERIALS CONTAINED IN TRANSPORT VEHICLES

BACKGROUND OF THE INVENTION

1. Field of the Invention

The present invention is concerned with an automatic sampling device for bulk materials in powder, granular or liquid form in containers carried by automobile vehicles such as tank lorries or wagons using a mobile sampling probe, and a process for putting such a device into operation.

2. Description of the Prior Art

In the domain of industrial product quality control, it is well known to take samples in order to verify the conformity of the products with the established standards.

Up till now, in the case of the quality control of products in bulk in tank lorries or similar, comprising in general several separate compartments, an operator carries out the control manually by introducing what is called a sampling tube successively into the different manholes of the compartments of the tank.

This sampling technique naturally presents various important inconveniences.

On the one hand, this type of manual sampling is inexact, because, with the operator introducing the sampling tube by hand, he does not know exactly at what depth it is immersed in the bulk product, and for this reason, the quality of the sample is random.

In addition, such manual operations, even when carried out by several operators, take a certain time, and it is not always possible to check all the tanks, unless a number of operators is available to sample simultaneously the different tanks, which would always be onerous.

It is to be noted that such controls are applied to a large number of important products of industry and commerce, such, for example, as milk products, flour, milled products, starch, animal food-stuffs, sugar, salt, cocoa, and also cement, plaster, liquid chemical products, fuels and also even wines, oils, etc.

That is why the present invention has the purpose of permitting a strict and precise control of samples, enabling also a saving of precious time and the taking of more representative samples both from the qualitative and quantitative view-points.

SUMMARY OF THE INVENTION

This problem is resolved in accordance with the invention by a sampling device of the type indicated above, characterized in that it consists of a moving gantry, running on rails between which the vehicle can be brought, and of which the upper transverse beam carries mobile means of support and movement of the sampling probe, means for applying suction to the sampling probe so as to draw the product towards a temporary receiver, and a sampler device for the product connected to the said receiver, these various parts being carried by the gantry and connected to a control desk installed at the bottom of a column of the gantry.

According to a further characteristic of the invention, the means of support and movement of the sampling probe are constituted by a carriage able to move transversely along the beam of the gantry and carrying an adjustable system for raising and lowering the probe vertically, with guiding and stopping this latter at desired points at predetermined heights in the compartments of the vehicle container.

According to a further advantageous characteristic of the invention, the probe is of a type with a double envelope formed by a tubular external sleeve and an internal sampling tube, the annular space between the external tubular sleeve and the internal tube of the probe being connected to the output side of a blower, the air from which comes out at the bottom of the probe to fluidize the bulk product, while the upper extremity of the probe is connected to an aspirator through the intermediary of the receiver and an intervening filter, so as to draw the product from the tank into the receiver by suction.

Furthermore, according to a characteristic of the invention, this sampling device includes an automatically controlled change-over arrangement at the bottom of the receiver comprising two transfer tubes separated obliquely downwardly, of which the shorter one has its opening at the level of the upper part of the container, and the other, considerably longer, finishes above the sampler device arranged at the bottom of the side column of the gantry, near to the control desk.

The present invention is also concerned with a process for putting the automatic sampling device indicated above into operation, according to which the container is positioned under the gantry, the covers of the container are opened, the carriage carrying the probe is positioned on the axis of the tank by means of the control box; by selecting the number of samples, the order is given for automatically starting up the sampling device, the gantry is advanced so as to detect the first manhole of the container, with a delay in stopping the gantry after detection to allow the probe to be positioned centrally, the probe is lowered slowly depending on the resistance of the product to penetration, then after a delay following the descent of the probe, the change-over arrangement is switched to the sampler device for a preliminary false sampling with rinsing of the change-over arrangement and of the transfer tube opening above the sampler device, then the change-over arrangement is switched to the transfer tube opening above the container and the sampler device is adjusted by rotation for carrying to the first sampling, it is detected that the sampling device is adjusted to the desired position, the change-over arrangement is again switched to the transfer tube opening at the sampler device, the passage of the product between the change-over arrangement and the sampler device is detected, then the change-over arrangement is switched to the transfer tube opening above the container, and the sampler device is adjusted for taking a second sample, following which the probe is withdrawn rapidly, with or without stopping for a continuous or discontinuous taking of samples at the height to which it has been raised, then the probe is returned to the upper position, following which the gantry is advanced until a second manhole is detected, so as to carry out sampling in conformity with the cycle of operations previously indicated.

It will be observed that the device and the automatic sampling process as previously indicated offers various advantages.

To carry out sampling of the type indicated manually, it is necessary to devote a period of 40 minutes, while with the system in accordance with the invention, the sampling is done in a period of about 14 minutes, including opening the covers of the container.

Such a system guarantees in addition a constant and sure quality of the samples so taken.

Furthermore, such a system offers a very great interest, not only as regards the availability of a sample before discharging the container or the tank, against a possible refusal of the first material, but also as regards the possibility of improving the performances of laboratories provided with rapid analysis equipment (for example, plasma torch), while these same laboratories can be held up by too long sampling times with a manual mode.

The system according to the invention thus enables automatic sampling of a pre-programmed weight for laboratory analysis, while ensuring a contamination less than 2%, and this for all the manholes and for different heights of the container or the tank.

Other characteristics and advantages of the present invention will appear from the description given further on, taken with reference to the attached drawing.

DESCRIPTION OF THE PREFERRED EMBODIMENT

Figure 1:
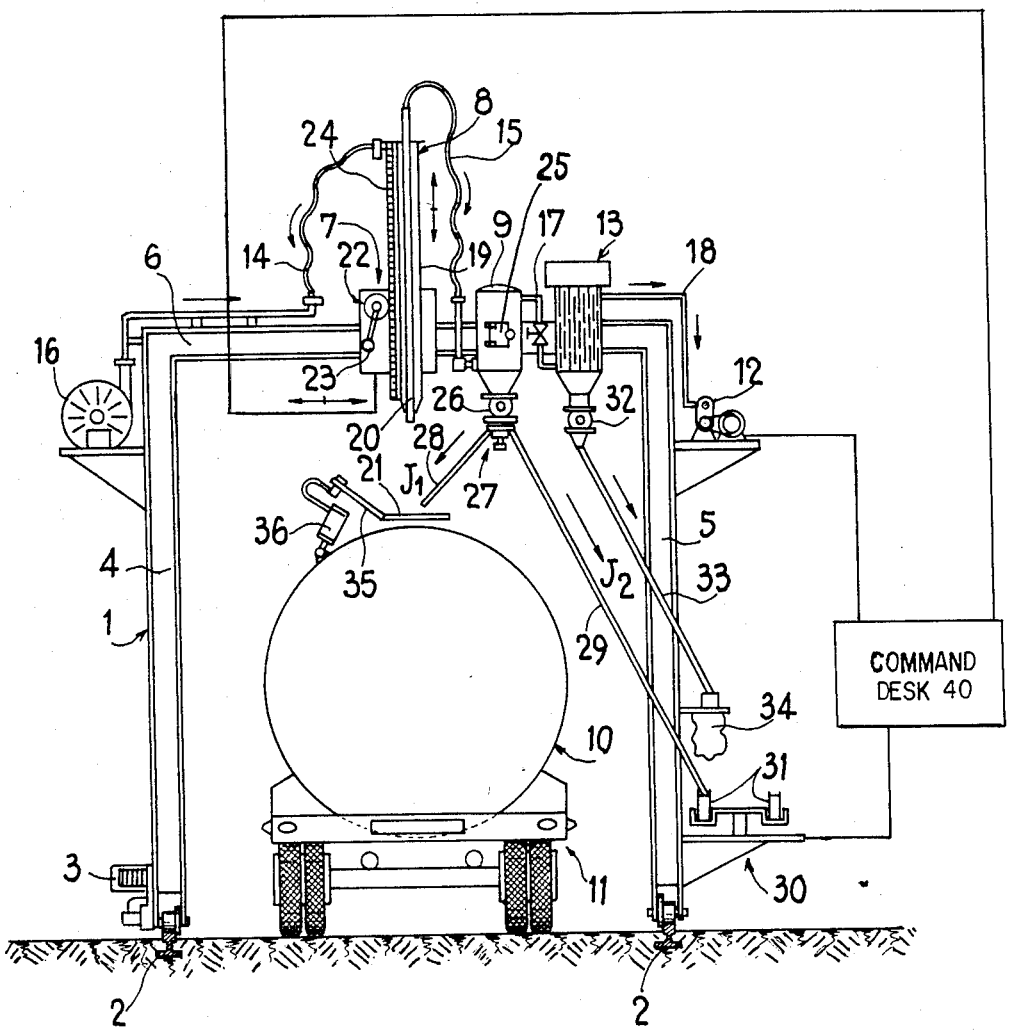
FIG. 1 illustrates an elevation view of the front face of the automatic sampling device according to the invention.

The automatic sampling device according to the invention is composed of a gantry designated as a whole by the reference 1, which is mounted on two parallel horizontal rails 2 placed on the ground, and is driven by an electric motor 3 for forward and backward movement, that is to say, perpendicularly to the plane of the drawing.

This gantry 1 comprises two vertical columns 4 and 5, connected at their upper part by a horizontal beam 6 on which are mounted movable means, designated as a whole by the reference 7, for the support and movement of a vertical sampling probe, designated as a whole by the reference 8, the means being preferably a carriage.

On this gantry there is fixed, in a way not shown in detail, a receiver 9 for the temporary reception of a bulk product drawn from a container such as the tank 10 carried by a lorry of which the chassis is indicated as a whole by the reference 11.

In addition, the beam 6 of the gantry 1 supports means 12 for putting the sampling probe 8 under suction, which consists of an electrically driven aspirator which is connected to the receiver 9 by the intermediary of a filter 13 also attached to the gantry.

Flexible tubes 14 and 15 respectively connect a blower 16 mounted on the vertical leg 4 of the gantry and the receiver 9 to the probe 8, in a manner described more in detail further on.

In addition, a pipe 17 connects the upper part of the receiver 9 to the lower part of the filter 13 and a pipe indicated by the reference 18 connects the upper end of the filter 13 to the aspirator 12.

The probe 8 has a double envelope, comprising a vertical external tubular sleeve 19 in which is mounted the actual vertical sampling tube 20, the upper part of which is connected by the flexible tube 15 to the receiver 9 and from there, through the intermediate filter, to the aspirator 12.

In the probe 8, between the external tubular sleeve 19 and the internal tube 20 there is an annular space which is connected to the end of the flexible tube connected to the blower 16, such that the product around the probe is fluidized when this latter descends into the tank 10 through the opening or manhole 21 provided in its upper part.

The probe group 8 is driven by a motor indicated schematically at 22, with two speeds, a slow speed for the descent and a fast speed for raising the probe, the positioning of the probe being in addition controlled by a standard system of detection of lower and upper positions, not shown. The probe group 8 is itself supported by the carriage 7, enabling the probe to be centered in front of the manhole 21. The system of driving the vertical rise and fall of the probe 8 can, for example, be realized by means of a pinion 23 on the motor shaft meshing with a rack 24 attached to the external tubular sleeve 19 of the probe, in such a way that the probe 8 can be introduced into the tank 10 while being guided and adjusted in a central position and being able to be stopped at desired points, at predetermined heights or displaced vertically in a continuous movement.

A valve (not shown) fixed at the lower extremity of the probe 8 enables the depression created inside the tube 20 by the aspirator 12 to be adjusted.

The receiver 9 includes in addition, an inspection door 25 and carries at its lower extremity an output valve or shutter 26 which opens into a lower automatically switchable change-over device 27 comprising two transfer tubes separating obliquely downwards, one of which is short, referenced 28 and opens at the level of the upper part of the tank 10, and the other, considerably longer, referenced 29, ends above a rotary sampler device designed as a whole by the reference 30 and fixed at the bottom of the vertical column 5 of the gantry 1.

The sampler device 30 comprises removable receiver jars referenced 31.

Furthermore, the filter 13 has an output valve or shutter 32 at its lower extremity, for emptying the micro-fines recovered from the filter which fall through a lower oblique tube 33 into a bag represented schematically and referenced 34, which quantity of fine material recovered per sample should not exceed 10% of the weight of the latter.

Provision is also made at a suitable position on the side of the vertical column 5 of the gantry 1 for an electrical command desk 40 enabling the use of the whole of the gantry 1 and of its various equipments in an entirely automatic manner.

As can also be seen, the manholes 21 of the tank 10 include covers referenced 35, which can be opened automatically by means of jacks 36 fixed on the tank and coupled to the pneumatic control circuit of the vehicle 11.

Before describing in a detailed way the functioning of this device and the putting into operation of the associated automatic sampling process, it will be noticed that when the change-over arrangement 27 is switched to the position permitting passage into the transfer tube 28, and during the descent of the probe 8, the product sucked up by the probe 8 arriving by the tube 15 in the receiver 9 is re-cycled on the top of the tank 10, the purpose of which is to effect a sort of rinsing of the circuit "tube 20-pipe 15-receiver 9-valve 20", which was, for example, contaminated during a preceding sampling in a tank. In the other position of the change-over arrangement 27, corresponding to the use of the transfer tube 29 towards the sampler device 30, the product contained in the receiver 9 falls under gravity to the device 30.

It will also be noticed that the fact of providing the tanks with a system of jacks instead of the covers which are at present found in the manual system, is a useful complementary arrangement for the operation of the automatic sampling system according to the invention, it being given that jacks, such as 36, enable time to be saved in opening the covers, as well as providing for the safety of the personnel who no longer have to climb on the tank to open such covers.

The process will now be described for putting the automatic sampling device, previously described, into operation.

The automatic functioning system includes the following operational phases:

(1) Positioning of the tank 10 under the gantry 1
(2) Opening of the covers 35 of the tank 10
(3) Positioning of the carriage 7 which supports the probe 8 on the axis of the tank by means of the control box: selection of the number of samples to be taken.
(4) Setting the order of automatic operation of the sampling device, with
   (a) Carriage 7 in top position
   (b) Change-over arrangement 27 in tank position (passage into transfer tube 28)
   (c) Rotary sampler device 30 in "first sample" position
   (d) Blower 16 running
   (e) Valves 26 and 32 operated
   (f) Filter 13 working
   (g) Aspirator 12 working
   (h) Gantry 1 in starting position.
(5) Advance of the gantry 1 for detection of the first manhole 21, either by magnetic contact (reflex cell) or by any other appropriate standard system: Delay in stopping the gantry after detection in order to centralize the probe 8.
(6) Command for the descent of the probe 8 at slow speed, the descent being decided as a function of the resistance to penetration of the product.

It will be noted that in this case, the servocontrol is carried out either by an intensity control with cut-off at the maximum, or by a friction clutch system or by any other known standard system (not shown), the stopping point being determined by the drive torque. The instruction to descent is given after an adjustable delay so as to allow the fluidization of the product to take place, again enabling the descent of the probe 8 to the chosen sampling position. During this period of descent, the product is re-cycled on the top of the tank 10 by means of the valve or shutter 26 and change-over arrangement 27, in order to rinse the circuit, as previously indicated.
   (a) Delay 5 seconds, after stopping the descent, for switching the change-over arrangement 27 to the transfer tube 29 going to the sampler device 30, for the first false sampling; rinsing of the circuit 27, 29, 20.
   (b) Return switching of the change-over arrangement 27 to the tank.
   (c) Rotation of the sampler device 30 bringing it into the first sampling position.
   (d) Detection of the correct position of the sampler device 30.
   (e) Switching of the change-over arrangement 27 to the sampler device 30.
   (f) Detection of the passage of the product between the change-over arrangement 27 and the sampler device 30, the period of blocking the detector known and not represented on the figure corresponding to a volume of product sampled.
   (g) Change-over arrangement in the tank position
   (h) Rotation of the sampler device 30 to the position corresponding to the second sample.
(7) Withdrawal of the probe 8 at fast speed and stopping of the probe as a function either of taking a sample at a determined height, or of taking an average sample on the whole height of return of the probe. If it is a question of taking a separate individual sample, the possibility of switching the change-over arrangement is used, which enables a change-over to the tank to be made at each sampling and to cause the rotation of the sampler device 30, which gives all the flexibility which the user might require.
(8) Return of the probe 8 to the top position and closing of the valve 26.
(9) Beginning of a new cycle with advance of the gantry until the second manhole on the tank is detected.
(10) Same operational phases as at 4 to 9 above.
(11) At the end of the sampling, return of the gantry to the starting position, with:
   (a) Probe 8 at upper position
   (b) Blower 16 stopped
   (c) Aspirator 12 stopped
   (d) Valve 32 closed.
(12) Unstopping the filter 13, if a swollen joint provided on this latter is closed; operation delayed.

It will be noted that the whole installation can also be used with manual operation and that all the manoeuvres are possible, and that it is also possible to select in the automatic mode a re-sampling on a particular manhole 21. It will be noted, furthermore, that various safety systems are provided, in a standard way, and not shown on the drawing; both as regards the advance and return of the gantry 1, with a protection at the upper part by a cable or a safety cell or any other system, and as regards safety in the vent of an obstacle to the advance of the gantry, and this with a safety device provided on the two vertical columns.

In addition, end of travel safety is provided on the rails in front of and behind the gantry, as well as a safety system for the sideways movement of the carriage on the horizontal beam of the gantry.

It will be noted that the automatic sampling device according to the invention is of interest to all industries receiving and delivering materials in bulk, whether in powder, granular or liquid form.

It will be noted that instead of the aspirator 12, a compressor can also be provided, according to the state of the powder, granular or liquid material. Furthermore, in the case of products with a melting point above ambient temperature, it is only necessary to provide for heating the sampling tubes in order to avoid coagulation.

It can therefore be seen that the installation in accordance with the invention opens the door to continuous analysis and could interest in addition all manufacturers of laboratory analysis equipment.

I claim:

1. An automatic sampling device for sampling products in containers carried by at least one automobile vehicle using a mobile sampling probe, comprising:
   (a) a travelling gantry movably attached to at least two rails, having two columns and an upper horizontal beam, wherein mobile means for supporting and horizontally moving said mobile sampling probe are attached to said upper horizontal beam and wherein said at least one automobile vehicle can be brought between said at least two rails;

(b) means for applying suction to an interior of said mobile sampling probe for drawing said product towards a temporary receiver;

(c) sample receiving means for receiving said product connected to said temporary receiver; and wherein said means for applying suction and said sample receiving means are carried by said gantry and are connected to a control desk installed at a bottom portion of one of said columns of said gantry.

2. The automatic sampling device according to claim 1 wherein said product is provided in bulk amounts, said product being in powder, granular or liquid form.

3. The automatic sampling device according to claim 2 wherein said automobile vehicle is a tank-lorry.

4. The automatic sampling device according to claim 2 wherein said automobile vehicle is a wagon.

5. The automatic sampling device according to claim 1 wherein said means for supporting and horizontally moving said mobile sampling probe comprises a carriage which is capable of travelling along said horizontal beam of said gantry, said carriage carrying an adjustable system for vertically raising and lowering said mobile sampling probe, said mobile sampling probe being guided and stopped at desired points, at pre-determined heights within compartments of said container of said automobile vehicle.

6. The automatic sampling device according to claim 5 wherein said mobile sampling probe is of a double envelope type comprising:

(a) an outer tubular sleeve;

(b) an inner sampling tube;

(c) an annular space between said outer tubular sleeve and said inner sampling tube, said annular space being connected to an outlet side of a blower, wherein air from said blower is blown into a bottom portion of said mobile sampling probe to fluidize said product; and (d) an upper extremity of said sampling probe being connected to an aspirator for drawing said product from said container to said temporary receiver by suction, said temporary receiver and an intervening filter being connected between said aspirator and said upper extremity of said sampling probe.

7. The automatic sampling device according to claim 6 wherein said inner sampling tube is connected by a first flexible tube to a bottom portion of said temporary receiver, an upper portion of said temporary receiver is connected by a second flexible tube to a lower portion of said filter, and said temporary receiver comprises an inspection door.

8. The automatic sampling device according to claim 5 wherein said adjustable system for vertically raising and lowering said mobile sampling probe comprises:

(a) a pinion driven by a motor, said motor being fixed to said carriage and said carriage being electrically connected to said control desk; and (b) a vertical rack meshing with said pinion, and being carried by an outer tubular sleeve of said mobile sampling probe.

9. The automatic sampling device according to claim 1 further comprising an automatically switchable change-over arrangement at a bottom portion of said temporary receiver, said automatically switchable change-over arrangement comprising two transfer tubes separating obliquely downwards from said temporary receiver, a shorter one opening at the level of an upper part of said container and a considerably longer one finishing above said sample receiving means arranged at a bottom of the column near to said control desk.

10. A process for operating the automatic sampling device according to claim 9 comprising the steps of:

(a) positioning said container containing said product under said gantry;

(b) opening at least one cover of said container;

(c) using said control desk to position said carriage on which said mobile sampling probe is held along an axis of said container;

(d) selecting a number of samples to be drawn;

(e) adjusting automatic starting of said sampling device;

(f) moving said gantry to detect a first manhole of said container and delaying stopping movement of said gantry after said first manhole is detected so as to centrally position said mobile sampling probe;

(g) lowering said mobile sampling probe at a slow speed in response to resistance of said product to penetration;

(h) after a delay following the step of lowering said mobile sampling probe, switching said change-over arrangement to said sample receiving means to perform a first false sampling for rinsing of a circuit formed by said change-over arrangment and the transfer tube which opens above said sample receiving means, this tube hereinafter called the first transfer tube;

(i) switching said change-over arrangement to the transfer tube which opens above said container, this tube hereinafter called the second transfer tube;

(j) rotatably adjusting said sample receiving means for performing a first sampling;

(k) detecting whether said sample receiving means is adjusted to a desired position;

(l) switching said change-over arrangement again to said first transfer tube;

(m) detecting passage of said product between said change-over arrangement and said sample receiving means;

(n) switching said change-over arrangement to said second transfer tube opening above said container;

(o) adjusting said sample receiving means for taking a second sample;

(p) withdrawing said mobile sampling probe at a high speed, with or without stopping for continuous or discontinuous, respectively, sampling at various heights as said mobile sampling probe ascends;

(q) returning said mobile sampling probe to an upper position;

(r) advancing said gantry until detection of a second manhole; and (s) repeating the preceding steps.

11. The automatic sampling device according to claim 1 further comprising a filter connected at a top portion of said filter to an aspirator by a pipe, said filter including, at a lower extremity, an emptying valve connected to an oblique emptying tube, wherein said emptying tube feeds into a removable emptying bag on one side of one column of said gantry.

12. An automatic sampling device for sampling products in a container using a mobile sampling probe, comprising:
   (a) a movable gantry comprising two columns and an upper horizontal beam, said container adapted to be positioned under said gantry;
   (b) mobile means for supporting and moving said mobile sampling probe, said mobile sampling probe being movably attached to said movable gantry;
   (c) a temporary receiver for temporarily receiving a sample withdrawn from said container;
   (d) sample receiving means for receiving said product from said temporary receiver, said sample receiving means being carried by said gantry;
   (e) means for applying suction to said mobile sampling probe for drawing said product into said temporary receiver, said means for applying suction being carried by said gantry;
   (f) means for transferring said product from said temporary receiver alternately to said sample receiving means and said container; and
   (g) a control desk installed at a bottom portion of one of said columns for controlling said automatic sampling device.

13. The automatic sampling device according to claim 12 wherein said means for supporting and moving said mobile sampling probe comprises a carriage movably attached to said horizontal beam of said gantry, said carriage comprising an adjustable system for verticaly raising and lowering said mobile sampling probe wherein said mobile sampling probe can be stopped at desired points at pre-determined heights within compartments of said container.

14. The automatic sampling device according to claim 12 wherein said means for transferring said product comprises automatically switchable change-over arrangement positioned at a bottom portion of said temporary receiver, said change-over arrangement comprising:
   (a) a first short transfer tube, an open end of said first short transfer tube being adapted to be positioned at the level of an upper portion of said container;
   (b) a second long transfer tube, an open end of said second long transfer tube being adapted to be positioned above said sample receiving means, said sample receiving means being positioned at a bottom portion of one of said columns; and
   (c) means for alternately opening and closing said first short transfer tube and said second long transfer tube,
wherein said first and second transfer tubes separate obliquely downwards from said temporary receiver.

15. The automatic sampling device according to claim 12 wherein said mobile sampling probe comprises:
   (a) an outer tubular sleeve;
   (b) an inner sampling tube;
   (c) means defining an annular space between said outer tubular sleeve and said inner sampling tube, said means defining an annular space being connected to an outlet of a blower for receiving air from said blower to fluidize said product; and
   (d) an upper extremity of said sampling probe being connected to an aspirator for suctioning said product from said container to said temporary receiver, said temporary receiver and an intervening filter being connected between said aspirator and said upper extremity of said sampling probe.

16. The automatic sampling device according to claim 15 wherein said inner sampling tube is connected by a first flexible tube to a bottom portion of said temporary receiver, and upper portion of said temporary receiver is connected by a second flexible tube to a lower portion of said intervening filter, and said temporary receiver comprises an inspection door.

17. The automatic sampling device according to claim 15 wherein said filter is connected at a top portion of said filter to said aspirator by a pipe, said filter including at a lower extremity, an emptying valve connected to an oblique emptying tube which feeds into a removable emptying bag on one side of one column of said gantry for collecting fines which flow through said filter.

18. The automatic sampling device according to claim 15 wherein said adjustable system for vertically raising and lowering said mobile sampling probe comprises:
   (a) a pinion driven by a motor, said motor being attached to said carriage and said carriage being electrically connected to said control desk; and
   (b) a vertical rack meshing with said pinion, said vertical rack being carried by said outer tubular sleeve of said mobile sampling probe.

19. A process for operating an automatic sampling device for automatic sampling of a product stored in a container using a mobile sampling probe movably attached to a gantry, comprising the steps of:
   (a) aligning said container and said mobile sampling probe so that said probe may be inserted into said container;
   (b) descending said mobile sampling probe into said product through a manhole in said container;
   (c) suctioning off a first false sample as said mobile sampling probe is descending into said product using an aspirator connected to said mobile sampling probe, said first false sample being temporarily stored in a temporary receiver, said temporary receiver comprising a first transfer tube positioned over said container, a second transfer tube positioned over a sample receiving means and means for opening and closing said first and second transfer tubes;
   (d) during said step of descending, recycling a portion of said first false sample into said container on top of said product using said first transfer tube;
   (e) preparing said device for drawing a first true sample;
   (f) drawing said first true sample from said container using said aspirator, said first true sample being temporarily stored in said temporary receiver; and
   (g) transferring said first true sample to a sample receiving means using said second transfer tube;
   (h) withdrawing said movable sampling probe from said container;
   (i) repeating steps (a)-(h) for each manhole in said container.

20. The process according to claim 19 wherein said step of aligning said container and said mobile sampling probe comprises the steps of:
   (a) positioning said container containing said product under said gantry;
   (b) opening at least one cover of said container;
   (c) positioning a carriage, which movably supports said mobile sampling probe, along an axis of said container using a control desk;
   (d) selecting a number of samples to be drawn;

(e) adjusting automatic starting of said sampling device;
(f) moving said gantry to detect a first manhole of said container; and
(g) delaying stopping the movement of said gantry after said first manhole is detected so as to centrally position said mobile sampling probe over said first manhole.

21. The process according to claim 20 wherein said step of descending said mobile sampling probe comprises the step of lowering said mobile sampling probe at a slow speed in response to resistance of said product to penetration.

22. The process according to claim 21 wherein said step of recycling said first false sample comprises the steps of:
(a) opening said first transfer tube; and
(b) transferring said first false sample from said temporary receiver to said container through said first transfer tube.

23. The process according to claim 22 wherein said step of preparing said device for drawing a first true sample comprises the steps of:

(a) closing said first transfer tube;
(b) opening said second transfer tube;
(c) rotatably adjusting said sample receiving means to a desired position for receiving said first true sample.

24. The process according to claim 23 wherein the step of drawing said first true sample comprises the steps of:
(a) stopping the descent of said mobile sampling probe at a desired location;
(b) delaying further operations for a short period of time; and
(c) suctioning said first true sample from said product into said temporary receiver.

25. The process according to claim 24 wherein the step of withdrawing said movable sampling probe comprises the steps of:
(a) rotating said sample receiving means for receiving a second sample;
(b) withdrawing said mobile sampling probe at a fast speed; and
(c) returning said mobile sampling probe to its top position.

* * * * *